(12) United States Patent
Ford et al.

(10) Patent No.: US 9,677,028 B2
(45) Date of Patent: Jun. 13, 2017

(54) SEED OIL REFINEMENT

(71) Applicant: R.J. REYNOLDS TOBACCO COMPANY, Winston-Salem, NC (US)

(72) Inventors: Kyle Ford, Germanton, NC (US); John-Paul Mua, Advance, NC (US); Thaddeus Jude Jackson, High Point, NC (US); Terence McGeown, Kensington (CA)

(73) Assignee: R.J. Reynolds Tobacco Company, Winton-Salem, NC (US)

( * ) Notice: Subject to any disclaimer, the term of this patent is extended or adjusted under 35 U.S.C. 154(b) by 0 days.

(21) Appl. No.: 14/822,434

(22) Filed: Aug. 10, 2015

(65) Prior Publication Data
US 2017/0044464 A1    Feb. 16, 2017

(51) Int. Cl.
*C11B 3/06*  (2006.01)
*C11B 3/04*  (2006.01)
*C11B 3/10*  (2006.01)
*C11B 3/02*  (2006.01)
*C11B 3/00*  (2006.01)

(52) U.S. Cl.
CPC  *C11B 3/06* (2013.01); *C11B 3/04* (2013.01); *C11B 3/10* (2013.01); *C11B 3/001* (2013.01); *C11B 3/02* (2013.01)

(58) Field of Classification Search
None
See application file for complete search history.

(56) References Cited

U.S. PATENT DOCUMENTS

| 2,069,187 A | 1/1937 | Kraybill |
| 2,561,330 A | 7/1951 | Ayers |
| 2,786,858 A | 3/1957 | Vandervoort |
| 2,980,718 A | 4/1961 | Cavanagh et al. |
| 3,069,443 A | 12/1962 | Witte et al. |
| 4,049,686 A * | 9/1977 | Ringers ............ C11B 3/04 554/190 |
| 4,280,962 A | 7/1981 | Watanabe et al. |
| 5,248,799 A * | 9/1993 | Schmutzler ......... C11B 3/10 554/191 |
| 5,315,021 A | 5/1994 | Beharry et al. |

(Continued)

FOREIGN PATENT DOCUMENTS

| CN | 103087819 A * | 5/2013 | ............ C11B 3/00 |
| EP | 1 178 103 | 2/2002 | |

(Continued)

OTHER PUBLICATIONS

CN 103087819, Lu Shunzhong, et al., Method for refining tea seed oil, 2013, English translation, 5 pages.*

(Continued)

*Primary Examiner* — Yate K Cutliff
(74) *Attorney, Agent, or Firm* — Womble Carlyle Sandridge & Rice, LLP

(57) ABSTRACT

Methods for refining crude tobacco seed oils and the refined tobacco seed oils produced by such methods are provided herein. In particular, methods for reducing the amount of free fatty acids in the crude oil, for modifying the color of the crude oil, and for reducing any undesirable taste/odor associated with the crude oil are provided. The present invention further relates to the incorporation and use of such refined oil within various products.

14 Claims, 1 Drawing Sheet

(56) References Cited

U.S. PATENT DOCUMENTS

| | | | |
|---|---|---|---|
| 5,696,278 | A | 12/1997 | Segers |
| 6,797,172 | B2 | 9/2004 | Koseoglu et al. |
| 8,952,187 | B2 | 2/2015 | Kruidenberg |
| 8,956,853 | B2 | 2/2015 | Dayton et al. |
| 2006/0111578 | A1* | 5/2006 | Arhancet ........... A21D 13/0074 554/8 |
| 2007/0207244 | A1 | 9/2007 | Crank |
| 2010/0058655 | A1 | 3/2010 | Fogher |
| 2014/0073807 | A1 | 3/2014 | Arhancet et al. |
| 2014/0356295 | A1 | 12/2014 | Gerardi et al. |

FOREIGN PATENT DOCUMENTS

| | | |
|---|---|---|
| EP | 1 917 863 | 5/2008 |
| WO | WO 00/19832 | 4/2000 |
| WO | WO 2006/009676 | 1/2006 |
| WO | WO 2010/093229 | 8/2010 |
| WO | WO 2010093229 A1 * | 8/2010 |
| WO | WO 2014/066097 | 5/2014 |

OTHER PUBLICATIONS

WO 2010093229, Mikhailovich, O., Method for produing tobacco oil, 2010, English translation, 3 pages.*

Wiedermann, L.H., Degumming, Refining and Bleaching Soybean oil, 1981, JAOCS, vol. 58, pp. 159-165.*

Carlson et al., "Degumming and Bleaching of *Lesquerella fendleri* Seed Oil," *J. American Oil Chemists' Society*, vol. 70, No. 6, 1993.

Desai et al., "Degumming of Vegetable oil by Membrane Technology," *Indian J. Chem. Tech.*, 9:529-534 (2002).

Bulletin 339, "Chemical Investigations of the Tobacco Plant, III. Tobacco Seed" *Connecticut Agricultural Experiment Station*, 1932.

Frega et al., Chemical Composition of Tobacco Seeds (*Nicotiana tabacum* L.) *JAOCS*, 68, 29-33 (1991).

List et al., "Supercritical CO2 Degumming and Physical Refining of Soybean Oil," *J. Am. Oil Chem. Soc.* 70(5): 473-476 (1993).

Giannelos et al., "Tobacco Seed Oil as an Alternative Diesel Fuel: Physical and Chemical Properties," *Industrial Crops and Products* 16(1): pp. 1-9 (2002).

Jude, "Extraction, Characterization and Industrial Applications of Tobacco Seed Oil (*Nicotiana tabacum*)" *Chemisty and Materials Research*, vol. 3(2): pp. 2224-3224 (2013).

Mukhtar et al., "Fatty Acid Composition of Tobacco Seed Oil and Synthesis of Alkyd Resin," Chinese J. Chem. 25(5): pp. 705-708 (2007).

Patel et al., "Production Potential and Quality Aspects of Tobacco Seed Oil," *Tob. Res.*, 24, 44-49 (1998).

Stanisavlievic et al.,"Comparison of Techniques for the Extraction of Tobacco Seed Oil," *Eur. J. Lipid Sci. Technol.*, 111, 513-518 (2009).

Stanisavlejevic et al. "Ultrasonic Extraction of Oil From Tobacco (*Nicotiana tabacum* L) Seeds," *Ultrasonics Sonochemistry* 14(5): pp. 646-652 (2007).

M. Abbas Ali, et al., "Comparative Study on Characteristics of Seed Oils and Nutritional Composition of Seeds from Different Varieties of Tabacco (*Nicotiana tabacum* L.) Cultivated in Bangladesh," *Asian Journal of Biochemistry*, 2008, pp. 203-201, vol. 3, No. 4.

Moldoveanu et al., "Dual Analysis of Triglycerides from Certain Common Lipids and Seed Extracts," *J. Agric.Food Chem.*, 59, 2137-2147 (2011).

Moldoveanu, "5. Profiling of lipids from fruit and seed extracts", Lipidomics: Sea Food, Marine Based Dietary Supplement, Fruit and Seed, 2012: pp. 73-123, Ed. Su Chen [online], Retrieved from the Internet, [retrieved Oct. 21, 2014], <URL: http://www.trures.com/ebook/uploads/suchencontent/T_13743193085')/020Su%20Chen.pdf>.

* cited by examiner

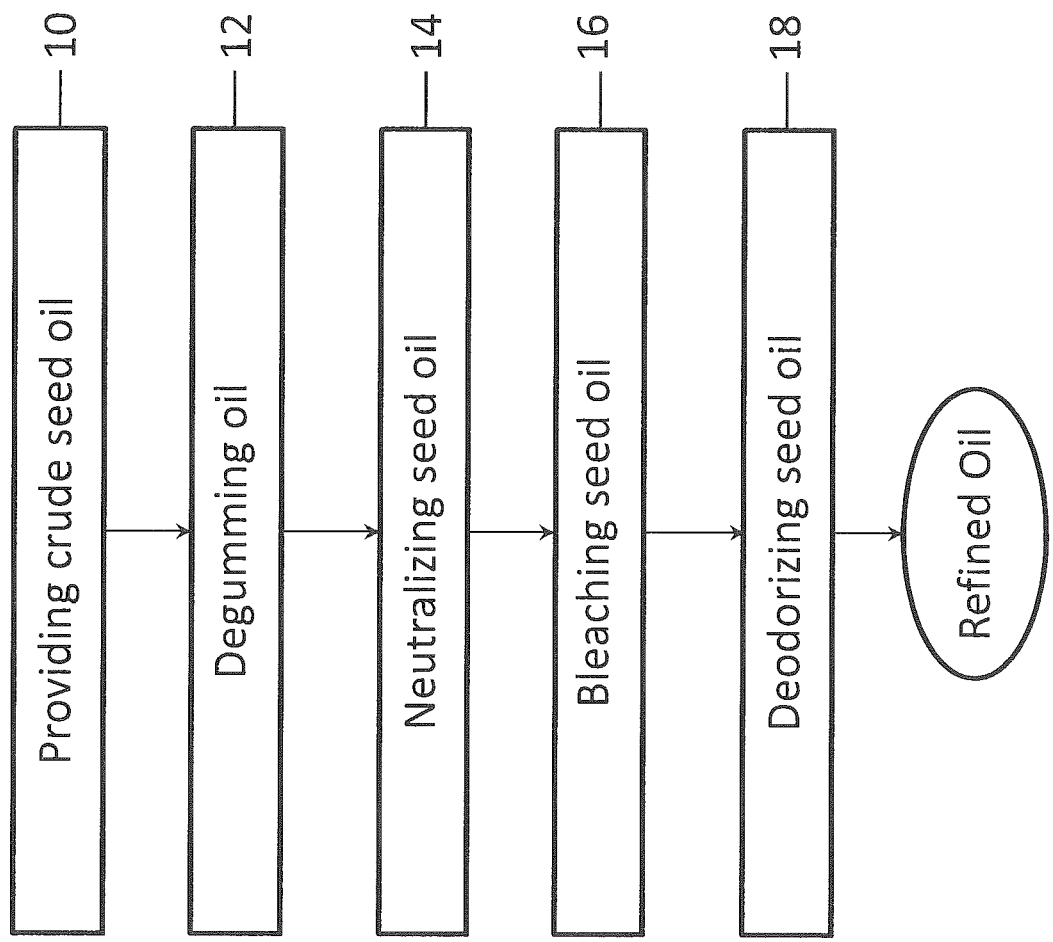

SEED OIL REFINEMENT

FIELD OF THE INVENTION

The present invention relates to methods of treating oils derived from tobacco. Of particular interest are oils obtained or derived from plant seeds or portions of plant seeds from the *Nicotiana* species.

BACKGROUND OF THE INVENTION

Seed oils are widely used for a variety of applications. For example, certain seed oils (e.g., sunflower oil, canola oil, sesame oil, cottonseed oil) are edible and are used for cooking and baking. Some seed oils are used in animal feed (e.g., cottonseed oil). Some seed oils are used for therapeutic purposes and/or as dietary supplements (e.g., in the form of consumable liquid or capsule forms). Some seed oils provide benefits in personal care products such as topical cosmetic formulations (e.g., lotions, gels, creams, shampoos, conditioners, tonics, styling products, and makeups). Certain seed oils are used as lubricants and/or as fuels (e.g., as biodiesels). Additionally, some seed oils find use in various commercial products such as paints, varnishes, putties, sealants, and the like. Although seed oils can be used directly (i.e., in as-harvested, "unprocessed" form), seed oils generally decompose rapidly and thus are commonly processed (e.g., "refined") for storage and use.

Tobacco seeds comprise a significant amount of oil. It has been noted that tobacco seed oil has properties comparable to other vegetable oils and holds promise for various applications, e.g., as a substitute for diesel fuel, as a component of cosmetic products, as a shoe polish, and as a reaction component for the production of alkyd resins. See U.S. Patent Application Publication No. 2014/0356295 to Gerardi et al., Jude, Chem. Mat. Res. 3(2): pp. 2224-3224 (2013); Mukhtar et al., Chinese J. Chem. 25(5): pp. 705-708 (2007), and Giannelos et al., Ind. Crops and Products 16(1): pp. 1-9 (2002), which are incorporated herein by reference. It would be desirable to provide methods for modifying the properties of crude tobacco seed oils to render them useful for these and other applications.

SUMMARY OF THE INVENTION

The present invention relates to methods for processing crude oil obtained from a plant seed (e.g., a tobacco plant seed) to modify one or more of the properties thereof. For example, in some embodiments, the amount of free fatty acids contained within the crude oil can be modified (e.g., reduced), the color of the crude oil can be modified (e.g., to provide a clearer oil), and/or any undesirable taste/odor associated with the crude oil can be minimized by the methods described herein. The present invention further relates to the incorporation and use of such refined oil within various products.

In one aspect of the invention is provided a method of refining a crude oil derived from a seed of a plant of the *Nicotiana* species, comprising: a) treating the crude oil derived from a seed of a plant of the *Nicotiana* species with acid; b) neutralizing the acid-treated oil with a basic aqueous solution and separating a precipitate from the oil to give a neutralized oil; and c) bleaching the neutralized oil, deodorizing the neutralized oil, or both bleaching and deodorizing the neutralized oil, to provide a refined tobacco seed oil comprising less than about 5% free fatty acids by weight. In some embodiments, the treating step provides a degummed oil with a decreased content of non-hydratable phospholipids (e.g., due to the dissociation of at least a portion of such phospholipids in the presence of the acid).

In certain embodiments, the acid comprises citric acid. In certain embodiments, the basic aqueous solution comprises sodium hydroxide. The neutralizing step, in some embodiments, is advantageously conducted with minimal agitation of the degummed oil with the basic aqueous solution. The neutralizing step may, in some embodiments, further comprise washing the neutralized oil with water. In some embodiments, the neutralizing step provides a neutralized oil with a lower phospholipid and phospholipid dissociation product content than that in the oil prior to the neutralizing step, as such components may be removed from the oil in the form of the precipitate generated and removed during the neutralizing step.

The bleaching step can comprise, for example, contacting the oil with at least one of bleaching clay and activated carbon. In one embodiment, the bleaching step comprises contacting the oil with both bleaching clay and activated carbon in a weight ratio of between about 2:1 and about 10:1 bleaching clay:activated carbon. In some embodiments, the bleaching step comprises contacting the oil with at least two bleaching clays, wherein the at least two bleaching clays have different pH values. Such at least two bleaching clays can, in some embodiments, remove different materials from the oil at this stage. The deodorizing step can, for example, comprise heating the neutralized oil at an elevated temperature at a pressure below atmospheric pressure. In one embodiment, the elevated temperature is about 150° C. or greater and the pressure is about 5 mm Hg or below.

In some embodiment the disclosed method further comprises obtaining the crude oil via extraction from a seed of a plant of the *Nicotiana* species. For example, the obtaining can comprise: solvent extraction of the seed and separation of the crude oil from an extracted seed; application of pressure to the seed to expel the crude oil; or a combination thereof. The refined tobacco seed oil provided according to the methods described herein can, in certain embodiments, be substantially colorless and/or substantially odorless.

In some embodiments, the method can further comprising determining the content of free fatty acid in the crude oil and calculating an amount of basic aqueous solution to use in step (b) based on the content of free fatty acid in the crude oil, the amount of acid added in step (a), and the desired maximum percentage of free fatty acids by weight in the neutralized oil. Based on such a calculation, in some embodiments, the moles of base in the basic aqueous solution can, in some embodiments, be in an amount of about 95% of the moles of free fatty acid plus the moles of acid added to about 100%/o of the moles of free fatty acid plus the moles of acid added (i.e., equivalent to the number of moles of free fatty acid plus the moles of acid added).

In another aspect of the present invention is provided a method of refining a crude oil derived from a seed of a plant of the *Nicotiana* species, comprising: a) treating the crude oil derived from a seed of a plant of the *Nicotiana* species with acid; b) neutralizing the acid-treated oil with an aqueous solution of sodium hydroxide, separating a precipitate from the oil to give a neutralized oil, and washing the neutralized oil with water; c) bleaching the neutralized oil by contacting the neutralized oil with one or more bleaching agents and separating a bleached oil from the bleaching agent; and d) deodorizing the bleached oil by heating the bleached oil, to provide a refined tobacco seed oil comprising less than about 5% free fatty acids by weight.

In a further aspect is provided an oil derived from a tobacco seed, comprising less than about 5% free fatty acids by weight. In some embodiments, the oil comprises less than about 4% free fatty acids by weight, or less than about 3% free fatty acids by weight. The tobacco seed-derived oil can, in certain embodiments, be substantially colorless and/or substantially odorless. The oil can, in some embodiments, be substantially clear/transparent (i.e., not hazy). In some embodiments, the disclosure further provides a product comprising a refined oil as described herein, wherein the product is selected from the group consisting of a cooking oil, dietary supplement, soap, detergent, paint, shoe polish, resin, personal care product, lubricant, and fuel.

BRIEF DESCRIPTION OF THE DRAWING

In order to provide an understanding of embodiments of the invention, reference is made to the appended drawing, which is not necessarily drawn to scale, and in which reference numerals refer to components of described exemplary embodiments of the invention. The drawing is exemplary only, and should not be construed as limiting the invention.

FIG. 1 is a schematic illustration of steps associated with the methods disclosed herein for the processing of tobacco seed oils.

DETAILED DESCRIPTION OF THE PREFERRED EMBODIMENTS

The present inventions now will be described more fully hereinafter with reference to the accompanying drawing. The inventions may be embodied in many different forms and should not be construed as limited to the embodiments set forth herein; rather, these embodiments are provided so that this disclosure will satisfy applicable legal requirements. Like numbers refer to like elements throughout. As used in this specification and the claims, the singular forms "a," "an," and "the" include plural referents unless the context clearly dictates otherwise.

This disclosure generally provides methods for providing oils from tobacco seeds, processing (e.g., refining) such tobacco seed oils, and incorporating such processed tobacco seed oils into various products. Materials derived from tobacco seeds in any manner that contain a relatively high amount of triglycerides (e.g., greater than about 50% by weight) are referred to herein as "tobacco seed oils." Triglycerides are esters derived from glycerol and three saturated, partially saturated, and/or unsaturated fatty acids. Exemplary fatty acids associated with such triglycerides include palmitic acid, linoleic acid, oleic acid, caprylic acid, myristic acid, pentadecanoic acid, palmitoleic acid, heptadecanoic acid, heptadecenoic acid, elaidic acid, gamma-linolenic acid, arachidic acid, arachidonic acid nervonic acid, 11-eicosenoic acid, 8,11,14-eicosatrieonic acid, 11, 14,17-eicosatrienoic acid, 5,8,11,14,17-eicosopentanoic acid, heneicosenoic acid, lignoceric acid, 4,7,10,15,19-decosahexanoic acid, and stearic acid.

Tobacco seed oils can, in some embodiments, also include a variety of other compounds having beneficial flavor and aroma characteristics such as amino acids and various polyphenols. In addition, tobacco seed oils can contain components that are advantageously removed in some embodiments. For example, oils can contain solid particles, pigments (e.g., chlorophyll), waxes, gums, trace metals, and/or substances that affect the odor and flavor of the oil. Crude seed oils also generally comprise a significant amount of free fatty acids ("FFAs"), which can result from the separation of one or more fatty acids from a triglyceride (leaving, e.g., a diglyceride and a free fatty acid). As shown in FIG. 1, the present disclosure provides methods for removing one or more components of crude seed oil. The methods disclosed herein can encompass one or more of the process steps depicted therein for the provision, refinement, and use of tobacco seed oils.

The provision of a tobacco seed oil (FIG. 1, 10) can be accomplished in various ways. Tobacco seed oils are generally obtained via processing seed material (e.g., whole and/or partial plant seeds), namely, seeds of the plant of the *Nicotiana* species, which is the characteristic reproductive structure of the plant (e.g., seed producing structure). See, for example, Frega et al., *JAOCS*, 68, 29-33 (1991); Patel et al., *Tob. Res.*, 24, 44-49 (1998); Giannelos et al., *Ind. Crops Prod.*, 16, 1-9 (2002); Mukhtar et al., *Chinese J. Chem.*, 25, 705-708 (2007); and Stanisavljevic et al., *Eur. J. Lipid Sci. Technol.*, 111, 513-518 (2009), which are incorporated herein by reference. Advantageously, seeds subjected to treatment according to the methods disclosed herein are high quality seeds, which are largely unbroken (i.e., whole) and ripe.

The selection of the plant from the *Nicotiana* species from which the tobacco seed to be processed is obtained can vary. Although not intended to be limiting, certain exemplary species include Burley, Flue, Turkish, Rustica, Kurnool, and the like. Descriptions of various types of tobaccos, growing practices and harvesting practices are set forth in *Tobacco Production, Chemistry and Technology*, Davis et al. (Eds.) (1999), which is incorporated herein by reference. *Nicotiana* species can be derived using genetic-modification or cross-breeding techniques (e.g., tobacco plants can be genetically engineered or crossbred to increase or decrease production of or to other change certain components, characteristics or attributes). For example, the *Nicotiana* species can be selected on the basis of producing relatively numerous seeds or seeds that incorporate relatively high levels of specific desired components, and the like. Additional information on types of *Nicotiana* species suitable for use in the present invention can be found in US Pat. Appl. Pub. No. 2012/0192880 to Dube et al., which is incorporated by reference herein. Plants can be grown under agronomic conditions so as to promote seed and seed development and can be grown in greenhouses, growth chambers, or outdoors in fields, or grown hydroponically.

The seed is harvested from the *Nicotiana* species of plant, and the manner by which the seed is harvested can vary. The seed can be removed from the rest of the plant by cutting or breaking the so-called seed head or seed capsule from the rest of the plant. Typically, virtually all of the seed (e.g., the whole seed) can be harvested, and employed as such. The various seeds can be isolated using typical mechanical separation and collection techniques. The time of harvesting the seed during the life cycle of the plant can vary. For example, the seed can be harvested when immature, and as such, the inflorescence or flower head can be removed from the plant. Alternatively, the seed head or seed capsule can be harvested from the plant after the seed has reached maturity.

The post-harvest processing of the seed can vary. After harvest, the seed, or portion thereof, can be used in the harvested form (e.g., the seed can be used without being subjected to any curing and/or aging process steps). For example, the seed can be used without being subjected to significant storage, handling or processing conditions. In certain situations, it is preferable that the fresh seed be used virtually immediately after harvest. Alternatively, for example, seed can be refrigerated or frozen for later use, freeze dried, subjected to irradiation, yellowed, dried, cured (e.g., using air drying techniques or techniques that employ application of heat), heated or cooked (e.g., roasted, fried or boiled), or otherwise subjected to storage or treatment for later use. In some embodiments, the makeup of the seeds can be modified, e.g., by removing one or more components therefrom before treatment according to the present disclosure.

The provision of seed oil from a harvested seed can involve one or more initial steps of preparing the seeds (e.g., cleaning), cracking and dehulling the seeds (to obtain the seed "meat"), conditioning the seed meat (treating the seed meat to make it pliable), milling/flaking the seed meat (to provide a desired particle size and rupture oil bodies), and pressing and/or extracting the milled seed meat. See, for example, the method steps described in U.S. Pat. Appl. Publ. No. 2014/0073807 to Arhancet et al., which is incorporated herein by reference. Alternatively, the seeds can be directly processed by pressing and/or extracting the intact seed without removing the seed meat (eliminating one or more of the steps noted above) to give the crude seed oil.

Pressing the seed or seed meat involves placing the seed or seed meat under pressure (i.e., using mechanical means) to squeeze oil therefrom, giving an "expressed oil." This process, when conducted in the absence of application of heat, is commonly referred to as "cold pressing." It is noted that some seeds will generate heat from friction during the pressing process and, for some seeds, large amounts of heat can be generated. The cold-pressed oil can be separated from the seed material and directly processed as described herein or can be further purified by extraction.

Extracting the seed, seed meat, or cold-pressed crude oil involves bringing the material to be extracted into contact with a suitable solvent or mixture of solvents for a period of time and under conditions sufficient to extract the oil into the solvent. The solvent is preferably one in which the seed oil is soluble, generally a non-polar solvent (e.g., n-hexane, iso-hexane, petroleum ether, mixtures thereof, and the like). One of skill in the art is aware of various ways in which extractions can be conducted (e.g., batch or continuous). General methods of extraction for the removal of oil from seeds are disclosed, for example, in Stanisavlejevic et al., Ultrasonics Sonochemistry 14(5): pp. 646-652 (2007) and Stanisavlejevic et al., Eur. J. Lipid Sci. Tech. 111(5): pp. 513-518 (2009), which are incorporated herein by reference. The oil-containing extract is then separated from the extracted plant material and concentrated, giving a crude extracted seed oil.

Processing of crude seed oils (obtained by various methods 10) generally can include steps of degumming (12), neutralizing/alkali refining (14), bleaching (16), and/or deodorizing (18), as shown in FIG. 1. These steps are shown in succession; however, it is noted that, in some embodiments, one or more of these steps can be eliminated or taken out of turn (e.g., a refined oil can be provided without being degummed, or a material can be bleached before being deodorized, for example). It is further noted that, depending upon the specific process employed for the treatment of a given seed oil, two or more of these steps can be conducted in tandem (i.e., the degumming and neutralization can occur together, for example).

Oil refining techniques are known for various oils, e.g., soybean oil. See, e.g., J. Am. Oil Chem. Soc. 70(5): 473-476 (1993); U.S. Pat. No. 2,069,187 to Kraybill, U.S. Pat. No. 2,561,330 to Ayers, U.S. Pat. No. 2,786,858 to Vandervoort, U.S. Pat. No. 2,980,718 to Bean et al., and U.S. Pat. No. 3,069,443 to Sipos et al., which are all incorporated herein by reference. Such traditional refining techniques were found to not be directly applicable for the refining of the tobacco seed oils obtained as disclosed above. In fact, analysis of tobacco seed oils indicated that the tobacco seed oil comprises a significantly higher free fatty acid content. Although not intended to be limiting, it is believed that the presence of large amounts of free fatty acids in the tobacco seed oil are responsible for the significant loss of oil noted when traditional techniques typically employed for soybean oil were employed to refine tobacco seed oils. The techniques described herein for the refining of tobacco seed oils comprise a series of modifications to the "traditional" methods known for the refining of other oils, e.g., soybean oil. Certain important modifications include modifications to the degumming step (wherein a smaller amount of water is employed than traditionally used, in the form of an aqueous dilute citric acid solution) and the neutralization step (wherein the mixing is conducted in a gentler manner to avoid causing significant emulsion). Surprisingly, the method steps in combination as disclosed herein result in significantly less loss (e.g., at least 10 less percent loss, at least 15 less percent loss, or at least 20 less percent loss) of overall mass than the traditional methods. In other words, the yield of refined oil using the techniques disclosed therein can be significantly higher than that using techniques known for the refining of soybean oils.

It is noted that fresher oils (e.g., oils that have been more recently obtained from the tobacco seed and/or oils that have not been subjected to extended storage) may exhibit a greater yield of refined tobacco seed oil than older oils. Further, fresh oils can, in some embodiments, exhibit substantially lower free fatty acid content and/or can exhibit higher stability than older oils. In such embodiments, it may be possible to refine the oils by skipping the neutralization step and, instead, subjecting the oil, after degumming (12), directly to bleaching (16) and/or deodorizing (18) steps. The free fatty acids that may be present throughout the process can, in some embodiments, be removed during the deodorizing step (via exposure to elevated temperatures, a process referred to as "physical refining"). This physical refining (i.e., neutralizing during the deodorizing step) can, in certain embodiments, be advantageous as it can reduce neutral oil loss that can be associated with "chemical refining," i.e., via neutralizing/alkali refining step 14, as neutral oil can become trapped in the soap phase produced during this neutralizing step. Physical refining is not well suited for all oils and is particularly not suitable for oils containing high levels of free fatty acids (e.g., greater than about 2%, 3%, or 4% free fatty acids by weight).

Degumming 12 refers to the removal of "gummy" components from the crude seed oil. The gumminess associated with some crude seed oils can be associated with various components, including, but not limited to, carbohydrates, proteins, and nitrogen-containing compounds. One principal cause of gumminess in oils the presence of phosphatides in the oil, which are advantageously removed from the crude oil, as an initial step of the process in certain embodiments.

Some of the phosphatides are hydrated or hydratable and therefore oil-insoluble (resulting in the gummy precipitate often observed in crude oils). Hydrated or hydratable phosphatides can be removed where present in crude oil in some embodiments by treating the crude oil with water to hydrate the phosphatides, causing them to agglomerate, and then removing the agglomerated phosphatides from the oil. In such embodiments, the crude oil is combined with water for a period of time sufficient to hydrate the gummy material and/or to provide agglomeration of at least a portion of the hydrated, gummy material (e.g., at least about 5 minutes, at least about 15 minutes, or at least about 30 minutes, such as between about 5 and about 60 minutes or between about 10 and about 45 minutes). In some embodiments, temperature control can be important during the process, to ensure that the temperature is high enough to ensure separation of the hydrated gums from the viscous oil layer, but not so high that the hydrated gums become substantially soluble in the oil layer. Separation can be conducted through various means, including filtration, centrifugation, decanting, and the like, to give an oil with reduced hydratable phosphatides.

Other phosphatides commonly present in crude oil are not hydrated and non-hydratable and thus cannot generally be removed by water degumming. For the removal of such phosphatides, the crude oil can be treated with a reagent (e.g., an acid) to dissociate the phosphatides (rendering them more soluble in aqueous solutions and an aqueous solution can later be used to remove the phosphatides, e.g., during neutralizing step 14). Enzymatic degumming (e.g., by treatment with phospholipidase), soft degumming (using a chelating agent, e.g., ethylenediaminetetraacetic acid, EDTA), and membrane degumming are also known methods for degumming oils and can be employed in the context of the present disclosure in place of or in addition to the degumming methods disclosed herein. Further detail on such processes can be found, for example, in U.S. Pat. No. 8,956,853 to Dayton et al., U.S. Pat. No. 6,797,172 to Koseoglu et al., and U.S. Pat. No. 5,696,278 to Segers; and Desai et al., Indian J. Chem. Tech., 9:529-534 (2002), which are incorporated herein by reference. In some embodiments, the degumming can be conducted in air; in other embodiments, the atmosphere may be controlled (e.g., such that the degumming process is conducted in the presence of an inert gas to minimize oxygen concentration).

According to the present disclosure, tobacco seed oils are advantageously degummed by acid treatment, which can, in certain embodiments, be effective for removal of both hydratable phosphatides and non-hydratable phosphatides. Various acids can be employed, including but not limited to, citric acid, phosphoric acid, and combinations thereof. In certain embodiments, citric acid (e.g., dilute citric acid) is used. Advantageously, the amount of liquid (i.e., aqueous acid solution) can be minimized (e.g., such that significantly less liquid (e.g., water) is employed than traditionally used to degum oils). Although higher amounts of liquid can be used according to the presently disclosed methods, it is desirable in certain embodiments to use a lower amount of liquid than traditionally used. The amount of liquid employed can vary and the minimal amount that can be effectively used can, in some embodiments, be about 0.2% w/w (liquid/oil) or less. It is noted that, advantageously, in certain embodiments, liquid amounts below this value can be employed to degum the tobacco seed oils disclosed herein. Particularly where the tobacco seed oils are low in, e.g., magnesium and calcium, the liquid amounts can be low, e.g., less than about 0.2% w/w (liquid/oil), less than about 0.15% w/w (liquid/oil), or less than about 0.1% w/w (liquid/oil), such as between about 0.02% w/w (liquid/oil) and about 0.2% w/w (liquid/oil), e.g., between about 0.05% w/w (liquid/oil) and about 0.2% w/w (liquid/oil).

Generally, acid degumming treatment is conducted by heating the oil to elevated temperature (e.g., greater than about 30° C. or greater than about 50° C., such as between about 30° C. and about 100° C. or between about 50° C. and about 80° C., e.g., about 65° C.). The acid, generally in the form of a solution in water, is added and the mixture is agitated or stirred for a period of time sufficient to dissociate at least a portion of the phosphatides. Generally, following acid treatment, the acid-treated oil is not processed to remove component(s) therefrom. Rather, the species formed upon acid treatment (e.g., by the dissociation of the phosphatides) are removed from the oil in later stages (e.g., including, but not limited to, during the neutralizing step 14).

The seed oil can, in some embodiments, be neutralized (14, FIG. 1) prior to use (i.e., "chemically refined"), and this can be done following the degumming step or can be the first step in the preparation of the crude seed oil for use. As noted above, seed oils generally comprise some content of free fatty acids ("FFAs"). Free fatty acids are responsible, at least in part, for seed oil acidity, due to an $H^+$ group associated with a carboxyl group thereof. The presence of free fatty acids in seed oil is generally advantageously minimized. In certain embodiments, the disclosure provides methods for minimizing the overall amount of fatty acids and/or minimizing the amounts of one or more specific fatty acids. Particular fatty acids that can be advantageously minimized by the methods disclosed herein include, but are not limited to, palmitic acid, stearic acid, oleic acid, linoleic acid, nervonic acid, and combinations thereof.

Methods for neutralizing free fatty acids in oils are generally known, e.g., as disclosed in U.S. Pat. No. 8,951,592 to Schols et al., U.S. Pat. No. 5,356,544 to Zilberman et al., U.S. Patent Application Publication Nos. 2014/0073807 to Arhancet et al., and 2013/0287925 to Schols et al., which are incorporated herein by reference. As referenced above, both physical and chemical refining methods for the neutralization of free fatty acids are known. The refining of tobacco seed oils as disclosed with reference to this neutralizing step 14 focuses on the use of chemical refining methods; however, it is noted that in some embodiments, physical refining (e.g., using vacuum distillation to remove free fatty acids, e.g., at a later stage of the process, such as during deodorizing step 18) can be used in place of or along with the chemical refining method to neutralize the free fatty acid content of the oil. Again, selection of an appropriate method for such neutralization (i.e., chemical refining and/or physical refining) is determined based on the properties of the oil to be treated (e.g., the free fatty acid content thereof).

Chemical refining involves the treatment of oil with a basic substance (e.g., caustic soda (sodium hydroxide) or potassium hydroxide), resulting in reaction between the basic substance and free fatty acids present in the oil, producing soaps. The soaps can be extracted into an aqueous solution. Generally, an excess of basic substance must be used to ensure that all or substantially all of the FFAs present in the oil is reacted and can be effectively removed. However, treatment of an oil having high levels of fatty acid with large amounts of caustic soda in this manner can result in the formation of a gelatinous mass that can be difficult to separate from the neutral oil remaining. Further, in such cases, the crude oil may contain unusually high amounts of diglyceride oil due to the high degree of fatty acid loss from the oil. The presence of high amounts of diglycerides results in difficult separation, as the diglyceride oil is likely to form emulsions with water. As tobacco seed oil generally comprises a relatively high percentage of free fatty acids (e.g., at least about 10% or at least about 15% by weight, such as between about 15% and about 25% by weight), these issues must be taken into consideration.

In some embodiments, the neutralization of tobacco seed oil is conducted using a solution of base (e.g., sodium hydroxide) in water. The amount of base employed in this step can be calculated based on the amount of acid added during acid degumming (if any) and the concentration of FFA in the oil, as calculated prior to neutralization. Calculation of FFA content can be done by various means. In one embodiment, FFA is calculated using a titration method, wherein a small sample of the oil is titrated with a base (e.g., sodium hydroxide or potassium hydroxide) in the presence of an indicator (e.g., phenolphthalein) to determine the point at which the solution is neutral. FFA can then be calculated. In certain embodiments, the following formula is used: FFA %=(v−b)×N×28.2/w, where v is the volume in ml of titration solution, b is the volume in ml of the blank, N is the normality of the titration solution, and w is the weight of the sample of oil in grams. One exemplary method for the measurement of FFA is provided in American Oil Chemists' Society Official Method AOCS Ca 5a-40 (2009), which is incorporated herein by reference. Other methods for the determination of FFA concentration are known, e.g., Fourier transform infrared transmission spectroscopy (FTIR), Fourier transform near-infrared transmission spectroscopy (FT-NIR), and fluorimetric enzymatic assay.

The amount of base to be added to the tobacco seed oil to achieve the desired (target) FFA level can thus be calculated. The concentration of the base in the basic solution added can vary and in some embodiments, can be between about 5% by weight and about 20% by weight and, in one particular embodiment, the concentration is about 11% NaOH by weight in water. The target FFA level can vary, but is desirably very low. For example, in certain embodiments, the target FFA level is about 10% or below, about 8% or below, or about 5% by weight or below. In one particular embodiment, the target FFA level is about 5% by weight or below.

Chemical refining is commonly conducted at elevated temperature. Exemplary elevated temperatures can, in some embodiments, be at least about 50° C. or at least about 60° C. and, in some embodiments, can range between about 50° C. and about 105° C. (e.g., between about 50° C. and about 75° C.). Addition of the base to the tobacco seed oil is advantageously controlled, e.g., done in a gradual manner to ensure that contact between the oil and base is maximized and that the formation of emulsions between the oil and the aqueous base solution is minimized. Equipment suitable for this purpose would be recognized by one in the art and can include, for example, a sprayer (as opposed to an inline mixer that would strongly agitate the oil). The mixture is gently mixed (again, trying to avoid significant emulsification) and precipitation of soap (resulting from reaction between the FFAs and the base) generally begins immediately. The entire neutralizing step is advantageously conducted with minimal agitation of the degummed oil with the basic aqueous solution to avoid the formation of emulsions.

In preferred embodiments, it is beneficial to begin removing the soap immediately and throughout the process to ensure the remaining oil and base can effectively react. The method by which the soap is removed can vary; in some embodiments, the base-treated oil is centrifuged at various stages of reaction to remove the soaps by centrifugal separation. After the desired time of base treatment (which can vary, e.g., from about 3 minutes to about 120 minutes), the neutral oil is generally washed at least once with water to dissolve any remaining soap in the water, which can be separated from the oil (e.g., by centrifugation). In certain embodiments, the oil is washed with heated water (e.g., at a temperature of about 30° C. or higher, about 40° C. or higher, or about 50° C. or higher, such as between about 50° C. and about 80° C.). In some embodiments, the oil is washed at least three times with water at a temperature of 65° C., wherein the water is added in an amount of about 10% by weight based on the weight of oil to which it is added. Again, care should be taken to avoid extreme agitation, particularly during the earlier stages of neutralization (subsequent water washes can be agitated progressively more strongly in some embodiments). It is noted that these separation steps and/or water washing steps in certain embodiments are effective also at removing the species addressed and/or formed during degumming step 12 (i.e., hydratable phospholipids and dissociation products of the non-hydratable phospholipids).

The resulting oil is dried under vacuum to give a neutral tobacco seed oil. Advantageously, this neutral tobacco seed oil comprises less than about 5% by weight free fatty acids. At this stage, the oil is preferably substantially transparent (i.e., not substantially hazy/translucent), although it may be colored (e.g., including, but not limited to, yellowish in color). If haziness is noted, the neutral oil is advantageously subjected to further water washing to remove any remaining soap and provide a transparent oil. This step is important, as the presence of soap in subsequent treatment steps can negatively impact the effectiveness of such steps. For example, residual soap may bind to adsorbents used in bleaching and can decrease the color removal. It is noted that, even after one or more water washings, the oil may retain some degree of haze, as in certain embodiments, the haze remains until the oil is dried under vacuum.

The neutral oil can, in some embodiments, be subjected to further treatment steps, e.g., to remove color, odor, and/or flavor therefrom. As shown in FIG. 1, a bleaching step 16 can be employed for the removal of color from tobacco seed oil. Bleaching involves the physical and/or chemical interaction of an oil with a bleaching agent to improve its quality (e.g., color). Color can arise from various sources, including, but not limited to, chlorophyll present in the seed from which the oil was obtained. Generally, bleaching is done at an elevated temperature. Elevated temperatures result in decreased viscosity of the oil, providing for better dispersion of the bleaching agent within the oil. In particular embodiments, bleaching step 16 is conducted with the oil at a temperature of at least about 80° C. or at least about 90° C., such as between about 80° C. and about 125° C. or between about 95° C. and about 105° C. Bleaching is preferably conducted at reduced pressure (i.e., under vacuum). For example, the operating pressure in the vessel in which the bleaching is conducted is advantageously between about 50 and about 125 mm Hg (absolute). The pressure is typically a variable parameter that can be adjusted in various embodiments to provide the desired results. Conducting the bleaching under vacuum can provide the added benefit of removing moisture (which can be detrimental to the bleaching process).

The contact time between the oil and the bleaching agent can range, e.g., from 15 to 120 minutes, e.g., from about 30 to about 120 minutes, with a contact period of about 60 to about 90 minutes being particularly preferable in the presently disclosed process. It is noted that, depending upon the method of operation, these times can be scaled accordingly. For example, in batch systems (as opposed to continuous system), contact time tends to be longer due to the sequential nature of the batch process.

Bleaching agents that are useful according to the methods disclosed herein can be any sorbent sufficient to bind one or more colored materials that may be present in the neutral oil. Such agents are generally porous in nature and can include various natural and synthetic clays and earths. Earths are generally composed of one or more of three types of clay minerals, namely, calcium montmorillonite (bentonite), attapulgite, and sepiolite. Earths can vary in mineralogical structure and adsorptive properties (e.g., surface area, particle size distribution, porosity, and surface acidity). In some embodiments, clays and earths can be used in their natural form and in some embodiments, they may be treated (e.g., via acid treatment) to modify the properties thereof (e.g., to create surface area and porosity).

Bleaching clays/earths can have different properties and can, in some embodiments, serve different purposes. For example, bleaching clays can vary in pH and can vary in the types of materials they can bind. Exemplary bleaching clays/earths that can be used in the methods disclosed herein include, but are not limited to, Bleaching Earth (BASF SE, Germany), Pure Flo® Bleaching Earths (Natural™, Supreme™ and Perform® product families, Oil-Dri Corp., IL, USA); Refoil Earth (Baroda Earth Pvt. Ltd., Vadodara, India); Ashapura's Bleaching Earth (Ashapura Midgulf NV, Belgium); and Activated Fuller's Earth (HRP Industries, India). Other bleaching agents useful in the methods disclosed herein include activated carbon, alumina, silicon dioxide, silica-alumina, and aluminum silicates. Further traditional bleaching agents, e.g., peroxides, ozone, and the like can be employed in certain embodiments. In some embodiments, a filter aid may be added along with the bleaching agent.

In one particular embodiment, a mixture of bleaching agents is employed for the bleaching of tobacco seed oil, comprising a combination of activated carbon and bleaching clays. Exemplary ratios of bleaching clays to activated carbon are not limited, but in certain embodiments, bleaching clays and activated carbon can be employed in a weight ratio of between about 1:1 and about 10:1 bleaching clay: activated carbon (including a weight ratio of between about 2:1 and about 10:1, or between about 3:1 and about 5:1). In particular, in one embodiment, the bleaching agent comprises 1% activated carbon, 1% bleaching clay (Oil-Dri Perform® 5000 Bleaching Clay) and 3% bleaching clay (Oil Dri B-80 bleaching clay). The 5000 Bleaching Clay has a pH of about 2-3 and is effective in removing red color and chlorophyll from the oil. The B-80 Bleaching Clay has a neutral pH and is effective in removing actives and color from the oil. In a specific embodiment, this combination of bleaching agents is added to tobacco seed oil at 95° C.-105° C. and the oil is treated for about 60-90 minutes to provide promising decolorization of the oil.

The amount of bleaching agent added to the oil can vary and is generally an amount sufficient to remove at least a portion of the color associated with the unbleached oil. This amount should be limited so as not to remove compounds that are desirably maintained in the oil after bleaching (e.g., which provide oxidative stability to the oil). Preferably, an amount of between about 0.1 weight percent and about 5 weight percent of bleaching agent, based on the weight of the oil to be treated is used.

Following contact of the tobacco seed oil with a bleaching agent under relevant conditions, as described above, the bleaching agent can be removed from the oil (e.g., by filtration). It is noted that efficient removal of the bleaching agent is important, as residual bleaching agent can, in some embodiments, affect the efficiency of further oil processing steps (e.g., deodorizing step 18). Bleaching preferably results in a modification of the color of the oil. The target color of the bleached oil is substantially colorless (e.g., not substantially brown, yellow, or green). Again, the oil is preferably clear (i.e., substantially transparent, not substantially hazy) at this stage. The color and clarity of the oil can be evaluated, for example, by visual inspection of the oil, by using the Lovibond color scale, and/or by any other colorimetric method.

Deodorizing (step 18, FIG. 1) can be optionally conducted to remove compounds with strong odors and/or flavors from the oil, generally as a final step in the processing methods disclosed herein (although not limited thereto). Deodorizing generally involves subjecting the oil to significantly elevated temperatures to volatilize various undesirable constituents of the oil (including remaining FFAs). Such elevated temperatures are sufficient to volatilize the undesirable constituents and generally are at least about 100° C., at least about 120° C., at least about 140° C., at least about 160° C., or at least about 180° C. For example, deodorizing can be conducted at temperatures between about 140° C. and about 240° C., and preferably between about 180° C. and about 220° C. Deodorizing is generally conducted under reduced pressure (i.e., under vacuum). For example, the operating pressure in the vessel in which the deodorizing is conducted is advantageously between about 1 and about 10 mm Hg (e.g., about 5 mm Hg). Typically, a carrier gas (e.g., dry steam) is used for the removal of volatile compounds from the vessel in which the deodorizing is conducted.

In one particular embodiment, deodorizing comprises subjecting the tobacco seed oil to a temperature of between about 180° C. and about 200° C. for about 60-120 minutes under very low vacuum (i.e., about 5 mm Hg or below). It is noted that, because the process described herein is capable of achieving removal of the majority of FFAs prior to this deodorizing step (primarily in neutralization step 14), reasonably low deodorization times and deodorization temperatures can be employed.

After treatment, tobacco seed oils processed according to one or more of the method steps shown in FIG. 1 and described above can be packaged and stored for later use. Advantageously, the tobacco oil is cooled before packaging and is packaged under nitrogen.

The overall method, particularly the method comprising all of the steps shown in FIG. 1 can, in some embodiments, provide for at least a 50% decrease by weight (e.g., at least a 75% decrease by weight, at least a 90% decrease by weight, or at least a 95% decrease in weight) in free fatty acid from the crude oil to the final treated oil. For example, one representative crude tobacco seed oil comprising 26.6 percent free fatty acids by weight was processed according to the methods provided herein to give a refined tobacco seed oil comprising 1.9% free fatty acids by weight.

Tobacco seed oils processed according to the methods provided herein can be characterized as having low free fatty acid contents, e.g., less than about 5% by weight, less than about 4% by weight, less than about 3% by weight, less than about 2% by weight, or less than about 1% by weight in certain embodiments.

Tobacco seed oils processed according to the methods provided herein can exhibit various beneficial features as compared with crude tobacco seed oils. For example, processed tobacco seed oils can, in some embodiments, exhibit improved stability, improved sensory characteristics (e.g., odor and color), and improved flavor characteristics. Such improvements can, in some embodiments, be evaluated qualitatively. Such improvements can, in some embodiments be evaluated quantitatively. For example, stability can be characterized by comparing the properties of an oil at different time periods using a range of methods, including but not limited to, measurement of refractive index, viscosity, evaporation residue, thin layer chromatography, high performance liquid chromatography in combination with mass spectrometry, and pH. Stability can also be evaluated based on the Oil Stability Index (OSI) at a certain temperature. In such evaluations, oil is subjected to constant temperature and constant air flow (bubbled through the oil) at conditions to promote/accelerate controlled oil break down. Representative equipment useful for such evaluations is provided, for example, by Metrohm (Switzerland). The OSI, understood to be synonymous with the induction time, is determined by measuring the time that passes until oxidation takes place at a high rate (e.g., based on American Oil Chemists' Society standard AOCS Cd 12b-92 and/or ISO 6886). The oxidation can be determined, e.g., by measuring the conductivity of water into which oxidation products formed during the analysis are transported (by the constant air flow) and determining the point at which a sudden, strong increase in conductivity is observed.

The refined tobacco seed oils provided according to the present disclosure have various applications. For example, the oils can be used in cooking (as an ingredient or a cooking oil), as a nutritional/dietary supplement, as a material in the manufacture of various products (e.g., soap, detergent, paint, shoe polish, and various types of resins), as a personal care product (e.g., in the types of compositions disclosed in U.S. Patent Application Publication No. 2014/0356295 to Gerardi et al.) and to replace lubricants and fuels.

An exemplary system to conduct the processing steps described herein can comprise one or more units for the implementation of each processing step, which may be separate or can be an integrated system (e.g., an oil refinery). Generally, such systems can incorporate components to implement each processing step, including but not limited to, mixing tanks, agitators, centrifuges, filters, and the like. The system advantageously provides for adjustment and regulation of such parameters as temperature, pressure (e.g., vacuum), moisture level, absorbent addition, and steam). Advantageously the system can be run substantially in the absence of air/oxygen to ensure the quality of the oil during treatment.

Although the foregoing disclosure has focused primarily on refining tobacco seed oils, the methods disclosed herein can be generally applicable in other contexts, e.g., in refining other types of plant seed-derived oils. The methods can be particularly applicable to plant seed-derived oils containing relatively high amounts of free fatty acids. Such oils are not limited and can include, for example, cottonseed oil, grapeseed oil, pomegranate seed oil, pumpkin seed oil, sesame seed oil, corn seed oil, carrot seed oil, cranberry seed oil, rosehip seed oil, Evening primrose oil, sunflower seed oil, flaxseed oil, and the like.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

EXPERIMENTAL EXAMPLE

The present invention is more fully illustrated by the following example, which is set forth to illustrate the present invention and is not to be construed as limiting thereof. Unless otherwise noted, all parts and percentages are by weight, and all weight percentages are expressed on a dry basis, meaning excluding water content, unless otherwise indicated.

Crude tobacco seed oil is obtained by flaking the seeds into smaller pieces and transferring the flaked seeds to an extractor. Solvent (e.g., hexanes) is charged into the extractor and the flaked seeds are soaked for 1 hour and the solvent is then circulated for 2 hours. The miscella (i.e., mixture of solvent and oil) is pumped out through a filter of fine polypropylene cloth into a holding tank. Mixed tocopherol is charged to the holding tank (in an amount of 0.025% of expected final quantity of oil). Active carbon is charged to the holding tank (in an amount of about 3% of the charged raw material) and the material is mixed well. The material is then filtered, washed, and concentrated. It is concentrated, for example, at 65-70° C. without vacuum, stripped at 75-80° C. under vacuum to remove residual solvent (to less than 25 ppm) and filtered through a bed of sodium sulfate. The resulting oil is evaluated and the fatty acid content is as follows: 7.6% C16:0 (palmitic acid); 3.0% C18:0 (stearic acid); 14.4% C18:1 (oleic acid); 68.5% C18:2 (linoleic acid); and 0.1% C24:1 (nervonic acid), based on the overall weight of the oil.

The crude seed oil is treated to remove free fatty acids. The oil is treated with 0.2 weight percent citric acid relative to the weight of the seed oil (used as a 50% w/w citric acid solution in purified water) by combining the oil and citric acid solution and mixing at 65° C. The acidified oil is then neutralized with 11% NaOH solution in purified water. The amount of NaOH added is determined based on the free fatty acid content of the oil and the amount of citric acid added during the acidification step. For example, here, for 1000 kg of the oil, the addition is 220 L of 11% NaOH to give a target free fatty acid content in the oil of 5% by weight. The NaOH is added gradually such that oil content is maximized (e.g., by sprayer). The oil is gently mixed after addition of the NaOH to ensure full content. Aggressive agitation is avoided, as this might promote emulsification, which generally makes separation of the neutral oil difficult.

As the NaOH is added, precipitation is immediately observed; removal of the precipitate is begun shortly after mixing to facilitate reaction between the remaining oil and NaOH solution. The precipitate can be removed, e.g., by centrifugation. Once the separation of the precipitate has begun, the neutral oil is repeatedly washed with water (e.g., 10% purified water by weight added to the mixture, agitated, and removed). The agitation is very gentle in at least the first washing, to avoid the formation of emulsions. Subsequent washes can be conducted with higher agitation.

The neutral, washed oil is dried under vacuum. The oil at this stage is desirably transparent and at this stage is often yellowish (i.e., transparent yellow). Although desirably transparent, in some cases, the oil may be somewhat translucent/hazy (indicating residual precipitate in the oil). Further water washing is optionally conducted to eliminate or decrease the haziness.

The desirably transparent oil is optionally bleached, e.g., under vacuum at about 95-105° C. for between about 60 and about 90 minutes. The bleaching is conducted using a mixture of adsorbents, namely, 1% activated carbon, 1% Oil-dri Perform 5000 bleaching clay and 3% Oil-dri B-80 bleaching clay.

The bleached oil can be further treated by deodorization by heating the tobacco seed oil to a temperature of between about 180° C. and about 200° C. for about 60-120 minutes under very low vacuum (i.e., about 5 mm Hg or below).

The invention claimed is:

1. A method of refining a crude oil derived from a seed of a plant of the *Nicotiana* species, comprising:
   a) treating the crude oil derived from a seed of a plant of the *Nicotiana* species with acid to give an acid-treated oil;
   b) neutralizing the acid-treated oil with a basic aqueous solution to give a neutralized mixture and separating a precipitate from the neutralized mixture to give a neutralized oil; and
   c) bleaching the neutralized oil, deodorizing the neutralized oil, or both bleaching and deodorizing the neutralized oil, wherein the bleaching comprises contacting the neutralized oil with at least two bleaching clays, wherein the at least two bleaching clays have different pH values, to provide a refined tobacco seed oil comprising less than 5% free fatty acids by weight, wherein the method results in at least 10% less loss than traditional methods of refining crude oils.

2. The method of claim 1, wherein the acid comprises citric acid.

3. The method of claim 1, wherein the basic aqueous solution comprises sodium hydroxide.

4. The method of claim 1, wherein the neutralizing step is conducted with minimal agitation of the acid-treated oil with the basic aqueous solution.

5. The method of claim 1, wherein the bleaching step comprises contacting the neutralized oil with both the bleaching clay and activated carbon in a weight ratio of between about 2:1 and about 10:1 bleaching clay:activated carbon.

6. The method of claim 1, wherein the deodorizing comprises heating the neutralized oil at an elevated temperature at a pressure below atmospheric pressure.

7. The method of claim 6, wherein the elevated temperature is about 150° C. or greater and the pressure is about 5 mm Hg or below.

8. The method of claim 1, further comprising obtaining the crude oil via extraction from a seed of a plant of the *Nicotiana* species.

9. The method of claim 8, wherein the obtaining comprises: solvent extraction of the seed and separation of the crude oil from an extracted seed; application of pressure to the seed to expel the crude oil; or a combination thereof.

10. The method of claim 1, wherein the refined tobacco seed oil is substantially colorless.

11. The method of claim 1, wherein the refined tobacco seed oil is substantially odorless.

12. The method of claim 1, further comprising determining a content of free fatty acid in the crude oil and calculating an amount of basic aqueous solution to use in step (b) based on the content of free fatty acid in the crude oil, the amount of acid added in step (a), and the desired maximum percentage of free fatty acids by weight in the neutralized oil.

13. The method of claim 12, wherein the amount of basic aqueous solution, in moles of base, is about 95% of moles of free fatty acid plus moles of acid added to about 100% of moles of free fatty acid plus moles of acid added.

14. A method of refining a crude oil derived from a seed of a plant of the *Nicotiana* species, comprising:
   a) treating the crude oil derived from a seed of a plant of the *Nicotiana* species with acid to give an acid-treated oil;
   b) neutralizing the acid-treated oil with an aqueous solution of sodium hydroxide to give a neutralized mixture, separating a precipitate from the neutralized mixture to give a neutralized oil, and washing the neutralized oil with water;
   c) bleaching the neutralized oil by contacting the neutralized oil with one or more bleaching agents, the bleaching agents comprising at least two bleaching clays, wherein the at least two bleaching clays have different pH values and separating a bleached oil from the bleaching agent; and
   d) deodorizing the bleached oil by heating the bleached oil, to provide a refined tobacco seed oil comprising less than 5% free fatty acids by weight, wherein the method results in at least 10% less loss than traditional methods of refining crude oils.

* * * * *